(12) United States Patent
Sugiura

(10) Patent No.: US 6,475,735 B1
(45) Date of Patent: Nov. 5, 2002

(54) HUMAN BMP-2 PROMOTER AND METHOD FOR EXPLORING BONE-RELATED SUBSTANCE BY USING THE SAME

(75) Inventor: Takeyuki Sugiura, Tokyo (JP)

(73) Assignee: Biopharm Gesellschaft zur Biotechnologischen Entwicklung von Pharmaka GmbH (DE)

( * ) Notice: Subject to any disclaimer, the term of this patent is extended or adjusted under 35 U.S.C. 154(b) by 0 days.

(21) Appl. No.: 09/674,459

(22) PCT Filed: Apr. 22, 1999

(86) PCT No.: PCT/IB99/00735

§ 371 (c)(1),
(2), (4) Date: Nov. 13, 2000

(87) PCT Pub. No.: WO99/57261

PCT Pub. Date: Nov. 11, 1999

(30) Foreign Application Priority Data

Apr. 30, 1998 (JP) ............................................ 10-120172

(51) Int. Cl.[7] ........................ C07H 21/04; C07H 21/02; C12Q 1/68; C12N 15/00; C12N 15/85
(52) U.S. Cl. ........................ 435/6; 435/91.1; 435/91.2; 435/320; 435/325; 536/23.1; 536/23.5; 536/24.1; 536/24.33
(58) Field of Search ........................ 435/6, 91.1, 91.2, 435/320, 68.1, 325; 536/23.1, 23.5, 24.1, 24.33

(56) References Cited

U.S. PATENT DOCUMENTS 6,083,690 A * 7/2000 Harris et al. ................... 435/6
6,090,620 A * 7/2000 Fu et al. ...................... 435/325

FOREIGN PATENT DOCUMENTS

WO        9638590        12/1996

OTHER PUBLICATIONS

Israel (A PCR Primer (1995) Cold Spring Harbor Laboratory Press, pp. 453–461).*
Levis (A PCR Primer (1995) Cold Spring Harbor Laboratory Press, pp. 539–543).*
XP–002125595 Cloning . . . protein–2 gene pp. 443–440 Sugiura.
XP–002125596 Bone . . . distal promoter (6 pages).
XP–002125597 Expression of . . . Cell Differentiation (12 pgs).
XP–002125598 Production . . . cell system vol. 35. No. 5 4/95–pp. 957–963.
XP–002125599 Molecular . . . protein 6, Tamada et al. pp. 247–251 1998.

* cited by examiner

Primary Examiner—Kenneth R. Horlick
Assistant Examiner—Alexander H. Spiegler
(74) Attorney, Agent, or Firm—Bierman, Muserlian and Lucas

(57) ABSTRACT

The present invention provides a method for exploring low molecular weight compounds which regulate positively or negatively the expression of the human BMP-2 with reference to a reporter activity by using 5' upstream region gene containing the human BMP-2 promoter and an animal cell introduced with a recombinant expression vector which has been connected to an appropriate reporter gene. The low molecular weight susbtances and their derivatives obtained by the present method have morphogenetic activity and inhibiting activity for bone and cartilage through the expression of human BMP-2 and are useful as preventive or therapeutic agents for bone and cartilage diseases.

11 Claims, 3 Drawing Sheets

SEQUENCE LISTING

<160> NUMBER OF SEQ ID NOS: 4

<210> SEQ ID NO 1
<211> LENGTH: 6728
<212> TYPE: DNA
<213> ORGANISM: HUMAN
<220> FEATURE:
<221> NAME/KEY: misc_feature
<222> LOCATION: (1)..(6728)
<223> OTHER INFORMATION: Human BMP-2  5' upstream gene sequence
      including the intron region.

<400> SEQUENCE: 1

```
actagtaacc aagtgttact catgctaaaa agccaacagg cttctcaggg gagtcttatt      60
ttgaagacta taatcatttt ccagaagcat gtgctcattc aacccatatt tttgaaatct     120
accaagtgca aaagaaaatc acataagata aactcacatc tttctgagaa ccagaaccga     180
tggccttaat ttgcatgtat atagtaatac aaatttgcaa ccttttgttg tcttcacaca     240
tatcttctca tttattcttc acaacctcca tgagaagtca actgttagtc tctatagagt     300
attcatgagg gagccgaggc tatgagaatt tgttactgcc atagatcaga ggtccccaac     360
ccccgggcca tgaatagtac ttgtccatgg cctgttagga accccagggg gcaggtgagg     420
gagcattact gcctgagctc tgcctcctgt cagatcagca gcagcattag attctcatag     480
gagctcaaac cctactgtga actgcatgta tgagggatct aggttgcatg ctccttatga     540
gaacctaact aatgcctgac gatctgacgt ggaaccgttt catcctgaaa ccatcacccc     600
caacctggtc tgtagaaaaa ttttcctcca caaaactggt ccctggtgcc aaaatggttg     660
gggacctctg ctttagattg actgacccaa ctggtggcct ttctgatgaa atatccactg     720
tttggcaata taataaaagc tgggagaaga gaaggagaag gaggagaaag aggaggagaa     780
gaaaggcatc caaagtccta tttcttaaaa ccaggccata ttgcagacag aaggccaaag     840
aatacatttg aagatacata gagtgagtag caatcagaaa ctaagttcac acatgttatc     900
```

-continued

```
catttgacct tcatcatgtc agtctgaagc aagcaaacat atatttattt accccaatta    960
acagatgaaa tgaccatttt aaagtcagtc atccatgaca gaaccaggaa ttagaaccca   1020
ggtcacccaa ctacatctta gagtgttatc aacatagttt acagacataa cttaaggtgt   1080
acatcttaaa ctgtgtgaca gtctaatcaa tgcacaaaat tcattctttt taatttttaa   1140
gaagatgtag ttggtacttg ctgaaagcag ttgatcctga tttggccaac ttggcctagt   1200
ttctgatata aatcactcca cctctcccat cctttctacc atgtctaatc aaacaccaaa   1260
aaggaaaaca tttgattgac taaatgcttc tcttttgcct tggctccaag ttcctgtaaa   1320
aaaaacttca tccaggtaaa gtaagtaggg atggttatgg gtgtcaccct tgtaacaaag   1380
cgatatgtat gctaaaaagc aaagagggtt tctcagggca gttgccacag gtttccatgg   1440
aatgacaatt acaaggtaga tggatcacgt aatgcctgct gtgaacttta caatacatgg   1500
ggatcactat tttaatgttg atttgcataa tgtttggcct agcaagaaca atactgaatg   1560
ctaatagcta cagaatgcaa taaaatggaa tatcatgtga gctgaagtgc taaaattgct   1620
aaagtatgac tgtaagcagt taatttcatc ccgagtcttg tccacacaca atcaaatgca   1680
aatttccact atctcctgag aaactgccaa gagatgactg aaatggaata gcaacaacct   1740
cctttatgtg gaatcattat ctggtcatct ttgcttttttt acataacttg tctgtaccct   1800
ctgatgcatt tgaatttgca acttctacta tccctatctt aaacaactcc ccactcccac   1860
ctctgcccct tccacatttg ctggcagatg cactaagtct gataaactca gcaagactga   1920
atctcaccct ctgaactgaa aaactttgaa tggacctttg aaaacggtag aattgacaat   1980
ggttagctgc aagtgatatt ttcaaggcaa acagacactc tcccaaagta ttaaataacc   2040
cagcattcta agttgcaggt ggaaggtagc cattagtgaa gagagagaaa aaaaaaaga   2100
aatagctcgt ctgtatttag atttatcatt tctgactatt gctcttccct ggaaaacggg   2160
taggtacagt catcctgtac ttcgatccca aatcagtctc tggagactac ttatttattt   2220
atttatttat ttatggactt ctttctttca agcgttcgaa ctcatttcca ccacaagagg   2280
gcagccatct ctaaaaaaaa aaaaataggg ccaaaattta tgtaagttgt gcttggaaca   2340
agcattcagt agttcctcag aaatcataca ccctacataa aagagattct gcaatgggca   2400
gcactaacat gaaacagtgt tcagaagtac ccattttccc tcagattcta aactgacaag   2460
gtttccactt atcaggttat gaagttctaa agctgcaaga catccttgag gtcatcacag   2520
gatatttatt tattttttct tcgggtgcat ccaatagtta tcaacttttc ctcctctttta   2580
aaagctactt aaatctcatt gaagttttgt tttgttttgt ttttgaaatc taagtaatga   2640
gagaaacaat tgttaacttc tcaattaaac ttgataggaa aggaaataat ttcagaagcc   2700
ctgtgtccat gagtaggata tgttttattg cctccttgtt tgcggtgcaa tgactctgag   2760
tgacaatcaa cttctatagc acctttttt ttttttttca ggaaataaag tagcatgttc   2820
ctgaataatt cccccacccc cttttatttt cctggtagtc aggcttcctc caaaatacct   2880
tatttgacct ttatacctttt agaaacagca agtgcctaat tcgcctctgt gggttgctaa   2940
tccgatttac gtgagcggaa cctagtatta ttttagctcc cctaccgaaa aaataataca   3000
catggataat agttctatta ccagctcctg cttctgactt ttttctctct gtttcgcagg   3060
cccgatagct ctgggaaagc agaacttggc cttttccaaa aattttctgc ccttggtttt   3120
ggggatcatt tgggcaagcc cgaggtgctg tgcatggggg ctcctggaat cctgggaagg   3180
gcagaaagcc ttgcccccag actcatcgtg cagcagctct gagcagtatt tcggctgagg   3240
agtgacttca gtgaatattc agctgaggag tgacttggcc acgtgtcaca gccctacttc   3300
```

-continued

```
ttgggggcct ggtggaagag ggtggcgtag aaggttccaa ggtcccaaac tggaattgtc    3360
ctgtatgctt ggttcacaca gtgcgttatt ttaccttcct ctgagctgct aatcgcctgc    3420
ctctgagctg ggtgagataa atatcacaag gcacaaagtg attgtacaat aaaaaaatca    3480
aatccctccc atccatcctt cagtctgcca cacacgcagt ctacgttaca cacatgtcac    3540
gtaaagcagg atgacatcca tgtcacatac atagacatat tgaccgaaat gtggcccttc    3600
ggttgcatat attctcatac atgaatatat ttatagaaat atatgcacat attttgtat     3660 attggatata tttatgtaac tataaattta catgcgtatg gatatgaaaa taatgcata     3720 cacatttatg taaaaaaatt tgtacacatg catttacata tgtaaataca tacatctcta    3780
tgtattaatg tttaaaaaca ctcaatttcc agcctgctgt tttcttttaa ttttcctcct    3840
attccgggga acagaagcg tggatcccac gtctatgcta tgccaaaata cgctgtaatt     3900
gaggtgtttt gttttgtttt gtttttttgaa atcgtatatt accgaaaaac ttcaaactga   3960
aagttgaata acgggcccag cggggaaata agaggccaga ccctgaccct gcatttgtcc    4020
tggatttcgc ctccagagtc cccgcgaggg tccggcgcgc cagctgatct ctcctttgag    4080
agcagggagt ggaggcgcga gcgcccccct tggcggccgc gcgccccgcc ctccgcccca    4140
ccccgccgcg gctgcccggg cgcgccgtcc acacccctgc gcgcagctcc cgcccgctcg    4200
gggatccccg gcgagccgcg ccgcgaaggg ggaggtgttc ggccgcggcg ggagggagcc    4260
ggcaggggcg tcccctttaa aagcgcgag cgccgcgcca cggcccgccg ccgccgtcgc     4320
cgccgccgga gtcctcgccc cgccgcgctg cgcccggctc gcgctgcgct agtcgctccg    4380
cttcccacac cccgccggga ctggcagccg ccgccgcaca tctgccgcca cagcctccgc    4440
cggctacccg aacgttctcg gggccagcgc cgagtggatc accggggacc gcgaggcacc    4500
cgcgcgccgc agacccgcg cgggctggag cacccgcag agcgcgccac agcgccgtgg      4560
cctctgctgc ccggtgcgcc agagccgcgg acgggcgcag agcgccgggg actccggagc    4620
cgatccctag cgcgcgatgc ggagcaccta ctgcaggaga tcggggcct gggacgcgct     4680 ggccgaggtg tgatcggacc ccaggctagc cacaaagggc acttggcccc agggctagga    4740
gagcgagggg agagcacagc cacccgcctc ggcggcccgg gactcggctc gactcgccgg    4800
agaatgcgcc cgaggacgac gggcgccag agcccggtgc tttcaactgg cgagcgcgaa     4860
tgggggtgca ctggagtaag gcagagtgat gcgggggggc aactcgcctg caccgagat     4920 cgccgccgtg cccttccctg gacccggcgt cgcccaggat ggctgccccg agccatgggc    4980
cgcggcggag ctaggcggag cgccggaccc tcgaccccg agtcccggag ccgcccgcg      5040 cggggccacg cgtccctcgg gcgctggttc ctaaggagga cgacagcacc agcttctcct    5100
ttctcccttc ccttccctgc ccggcactct tcccctgct cgctgttgtt gtgtgtcagc     5160
acttggctgg ggacttcttg aacttgcagg gagaataact tgcgcacccc actttgcgcc    5220
ggtgcctttg cccagcggga gcctgttcgc catctccgag ccccaccgcc cctccactcc    5280
tcggccttgc ccgacactga gacgctgttc ccagcgtgaa aagagagact gcgcggccgg    5340
cacccgggag aaggaggagg caaagaaaag gaacggacat tcggtccttg cgccaggtcc    5400
tttgaccaga gtttttccat gtggacgctc tttcaatgga cgtgtcccg cgtgcttctt     5460 agacggactg cggtctccta aggtagagg acgcgggcca gggccggggt gggtggtggg     5520
tgggaggggg atttgggcag ccactgcggt agagcccttc cttacgtcca ggccagaagt    5580
aaacagaccc ctctccagtc cacgtgcaag gaggccctgc agggctccca cttccagctg    5640
```

-continued

```
cccgggcga ccgtaagcct caccctcccg gcccgcactc ttccacccct ctttcttccc    5700
ctctccctgg aatacttttg gagctgttaa cacttagatg aggtgtttta tttatttatt    5760
tatttatttt taatttttt aaaaactttt ttgggtcaaa gaaatcccct tgagagggta    5820 gccctggtt tcacccgtta gctgagaacc tgtccgctct gccatggtga tctccattct    5880
tcaagtgttt ccgggagact tggtttcttt gctcagagcc gtgtcccatt taggaaagta    5940
ctaggagttt ggggttctcc ctacttgttt ccagaaatgc gaggggtcag tactgaagga    6000
tcacttggta ctgtgttttt aacagctgac acgtgcatta atagatattc accatttacg    6060
taatcccggg aagatacatg tgtatcttga ctgcactgtg gggatgcggg atggagctgc    6120
ctttcgagac acccctgagg gtaggggcct gggacacaag tcataagtgg cttcagaagt    6180
tgtggccttg agcttacagg gtctggaagc tataagggtg tgtgtgtgtg tgtgtgtgtg    6240
tgtgtgtgtg tcaggaagtt ctatacagtg cctctaagga agtcacatgc accatttatg    6300
tgtgtttata tgccagacag cgctcagcac tccgcatttg ggtttgtata ggggacgcag    6360
ggtgtcagat caagcggtgg ttttcccagg ttcccggcat tggctgtcag cgctgtgtca    6420
cacacaaaaa agtgacagtc attggcgctg gtttggttgg gggggagggc aaatcccaaa    6480
tctgatgtca gacgagctaa gcgttggatg ggagcgataa atcatctggt tcaggaactt    6540 ggaccttc attatcccaa acgtttgagc ttcggtcggt cttacctaga ctcgtgagtg    6600
tgccaagcca ggagggcatc ctggaggagg cacgccagcc aaatgggaga ccgggccgcg    6660
ggggcgcgag gggggaggac tgggcgggga actcgggtga ctcacgtcgg tcctgtccgc    6720
aggtcgac    6728
```

<210> SEQ ID NO 2
<211> LENGTH: 23
<212> TYPE: DNA
<213> ORGANISM: HUMAN
<220> FEATURE:
<221> NAME/KEY: misc_feature
<222> LOCATION: (1)..(23)
<223> OTHER INFORMATION: Sense PCR primer B2-3 for screening human BMP-2
      gene corresponding to the exon of the coding
      region.

<400> SEQUENCE: 2
gttttgatgt cacccccgct gtg                                            23

<210> SEQ ID NO 3
<211> LENGTH: 23
<212> TYPE: DNA
<213> ORGANISM: HUMAN
<220> FEATURE:
<221> NAME/KEY: misc_feature
<222> LOCATION: Complement((1)..(23))
<223> OTHER INFORMATION: Reverse PCR primer B2-7 for screening human
      BMP-2 gene corresponding to the exon of the coding region.

<400> SEQUENCE: 3
cagctggact taaggcgttt ccg                                            23

<210> SEQ ID NO 4
<211> LENGTH: 60
<212> TYPE: DNA
<213> ORGANISM: HUMAN

```
-continued

<220> FEATURE:
<221> NAME/KEY: misc_feature
<222> LOCATION: (1)..(60)
<223> OTHER INFORMATION: Sense PCR  5'-digoxigenin labeled primer for
      Southern blotting corresponding to 5' upstream
      human BMP-2 gene region.

<400> SEQUENCE: 4
ggggacttct tgaacttgca gggagaataa cttgcgcacc ccactttgcg ccggtgcctt      60
```

HUMAN BMP-2 PROMOTER AND METHOD FOR EXPLORING BONE-RELATED SUBSTANCE BY USING THE SAME

This application is a 371 of PCT/IB99/00735 filed Apr. 22, 1999.

BACKGROUND OF THE INVENTION (1) Field of the Invention

The present invention relates to a 5' upstream region DNA containing a promoter of a human bone morphogenetic protein (hereinafter called BMP-2). Further, the present invention provides a method for exploring a low molecular weight compound positively or negatively which regulates the expression of human BMP-2 by using a mass of animal cells that are introduced with a 5' upstream region DNA containing the human BMP-2 promoter and a structure connected to a suitable reporter gene, and by using a reporter activity as an indicator.

(2) Description of the Related Art

Many substances have been known as usable for healing of bone deficit, fracture, etc. by inducing bone regeneration. Among them, BMP is a protein belonging to TGF (transforming growth factor) -β superfamily and has been formerly found as a substance inducing ectopic ossification and existing in a decalcified product of a bone (Trends in Biotechnol. 11: 379–383, 1993). BMP members known so far range from BMP-1 to BMP-14. Among them, the members from BMP-2 to BMP-14 have been known as showing the bone morphogenetic activity. BMP-2 has been known as having the strongest activity of bone morphogenesis (Science 242: 1528–1534). It has been known that recombinant BMP-2 induces ectopic ossification (Proc. Natnl Acad. Sci. USA 87: 2220–2224, 1990), and is effective to bone deficit in animal model (J. Bone and Joint Surg. 74A, 659–670, 1992). The BMP proteins, particularly ranging from BMP-2 to BMP-14, are effective to therapeutic and preventive treatments of various bone disturbances and bone diseases. However, the BMP proteins exist in very small quantity in nature, and for an available large quantity for therapeutic use, production of a recombinant protein is necessary. The production of the recombinant protein generally is very expensive rather than the preparation of a small molecular substance. Moreover, there are many restrictions as a medical drug in terms of physical properties or administration methods due to its proteinic characteristics. Considering these points, a low molecular organic compound having the equal activity to that of said BMP protein, if any, will become a highly promising medical drug.

For such an exploring method, an example was so far reported using a murine BMP-2 promoter (WO97/15308). The region of the murine BMP-2 promoter has been already cloned (Biochem. Biophys. Acta, Vol. 1218, p. 221–224, 1994), but no report has been published for the region of human BMP-2 promoter and an exploring method employing the human BMP-2 promoter. A comparison of the DNA sequence of 741 bp of the 5' upstream exon region of said murine BMP-2 promoter with the corresponding human BMP-2 promoter sequence (the base sequence No. from 4709 to 5483 shown in SEQ ID NO. 1 of the Sequence Listing) of the present invention shows 71.6% homology between these two sequences. Because all the materials used for establishing the exploring method presented by the present invention are of human origin, the substance discovered from exploration can be quite effective in clinical application.

SUMMARY OF THE INVENTION

The present invention provides a 5' upstream region DNA containing a promoter of human BMP-2. By using 5' upstream region gene containing the human BMP-2 promoter and an animal cell introduced with the recombinant expression vector which has been connected to an appropriate reporter gene, the low molecular weight compounds which regulate positively or negatively the expression of human BMP-2 can be explored with reference to a reporter activity. The low molecular weight compounds and their derivatives have morphogenetic activity and inhibiting activity for bone and cartilage through the expression of human BMP-2 and are useful as preventive or therapeutic agents for bone and cartilage diseases, remedies for osteometastasis, or therapeutic and preventive agents for osteohyperplasia.

DESCRIPTION OF THE PREFERRED EMBODIMENT

Figure 1:
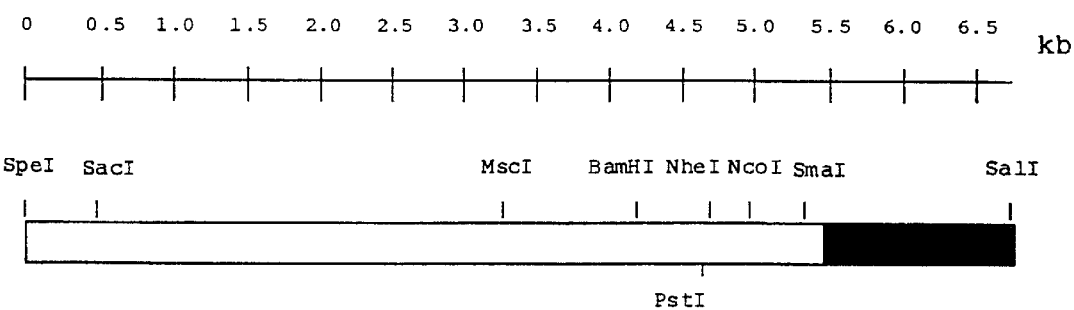
FIG. 1 is an exon-intron structure of 6.7 kb 5' upstream region of human BMP-2 gene and a restriction enzyme map. A solid black shows an intron region.

The present invention relates to a DNA containing a human bone morphogenetic protein-2 promoter region having a base sequence No. from 1 to 6728 shown in the SEQ ID NO. 1 of the Sequence Listing, or fragments thereof. The SEQ ID NO. 1 of the Sequence Listing shows the 5' upstream region sequence of the human BMP-2 gene.

The present invention relates to a method for preparing the DNA shown in SEQ ID NO. 1 of the Sequence Listing by conducting the following steps of:

(1) screening of a P1 phage human genomic DNA library by PCR method using a primer represented by SEQ ID NO. 2 and SEQ ID NO. 3 of the Sequence Listing, (2) digestion of the isolated P1 phage with restriction enzymes SalI and SpeI, (3) identification of the aimed fragment by Southern blotting, and (4) subcloning of the aimed fragment into pbluescript vector cut by the same enzymes.

The present invention relates to a recombinant expression vector characterized by integration of the DNA shown in SEQ ID NO. 1 of the Sequence Listing. The vector integrated is not restricted in particular and can be used among ones commercialized. As a preferable example, pGL3 basic vector (a product of Pro Mega Ltd.) was used. It was connected to the base sequence shown in SEQ No. 1 of the Sequence Listing which had been treated with a restriction enzyme. Then, pBMP2 (9660 bp) was obtained to be a recombinant expression vector of the present invention.

The present invention relates to a method for exploring a bone-related substance, characterized by using the full length or a part of DNA shown in SEQ ID NO. 1 of the Sequence Listing that is connected to a reporter gene. In other words, the present invention provides the method for exploring a substance that induces BMP-2, which is a member of BMP proteins. Since the substance obtained by the exploring method, although it is low molecular weight, has an effect on inducing an expression of human BMP-2, a bone formation factor, it is considered to have an effect equivalent to that of human BMP-2 and to be extremely useful.

In detail, a plasmid vector (above-described recombinant expression vector) is constructed to locate a suitable region of the 5' upstream region of the human BMP-2 gene shown in SEQ ID NO. 1 of the Sequence Listing in front of a reporter gene, and it is necessary to introduce the recombinant expression vector to mammalian cells, preferably human osteoblast-like cells, such as SaOS-2 cells, with a liposome. The animal cells stably transfected with the recombinant expression vector are selected by using a resistance marker. By such an exploring method, osteogenesis inducing or inhibiting substances can be explored.

The present invention also provides a method for exploring a substance, which inhibits the expression of human BMP-2. If human BMP-2 has some relationship with bone and cartilage hyperplasia, the hyperplasia diseases can be prevented by inhibiting the expression.

A low molecular weight compound which induces or inhibits the expression of human BMP-2 can be obtained by isolating the promoter which regulates the expression of the gene, by connecting it to a suitable reporter gene and by introducing the gene structure to a suitable mammal cell to make an exploring system. The reporter gene such as luciferase gene and β-galactosidase gene shows an expressing status on behalf of an original product. A substance regulating the expression of human BMP-2 in the exploring system works on the promoter to increase or decrease the expression level of the reporter gene. Therefore, a simple and easy measurement of the reporter activity makes an exploration of the aimed substance possible.

The animal cell transfected with said vector can be used for a method for screening a chemical compound library by high throughput screening (Nature, Vol. 384, Suppl., p. 14–16, 1996) and finding an active substance from natural substances. The substance which increases or decreases an activity is searched by treating the cells with a substance for an appropriate time period and afterwards measuring the reporter activity. The compound obtained hereby can regulate the expression by working directly on a transcription factor or indirectly on the promoter of human BMP-2 through regulating a signal transduction system. Therefore, these compounds are effective as a therapeutic agent for osteocartilaginous diseases, cancer metastasis to bone, or osteohyperplasia.

The substance obtained by the present invention has bone or cartilage morphogenetic activity and is effective as an agent for therapeutic and preventive treatment in the fields of orthopedic surgery (fracture, osteoarthritis such as joint osteoarthritis and hip joint osteoarthritis, arthrosteitis, damage of cartilage such as damage of meniscus, regeneration of bone and cartilage deficit caused by injury and tumor dissection, bone reconstruction such as spinal fusion and vertebral canal enlargement, and congenital cartilage and bone diseases such as dysoteogenesis and achondroplasia), or dental fields (bone reconstruction such as palatoschisis, mandible reconstruction, and residual ridge construction), and osteoporosis. Moreover, the substance of the present invention can be used for bone graft in aesthetic surgery. These therapeutic treatments are effective to therapies in the fields of veterinary surgery. On the other hand, the present invention can provide a substance which inhibits bone or cartilage morphogenesis. In this case, the substance is applied as an agent for prevention and therapy of bone and cartilage hyperplasia.

EXAMPLES

This invention shall be more illustratively explained by way of the following Examples.

Example 1
Cloning of Human BMP-2 Genomic DNA

PCR reaction was carried out by using a primer B2-3 shown in SEQ ID NO. 2 of the Sequence Listing and a primer B2-7 shown in SEQ ID NO. 3 of the Sequence Listing under the condition of 94° C. for 1 min, 60° C. for 30 sec, and 72° C. for 30 sec, and a human genomic DNA library of a P1 phage vector (a product of Genome System Ltd.) was subjected to screening. Under this condition, a 270 bp band occurs by using a human placenta genomic DNA as a template (a product of CloneTech). P21, one of 2 phage vector clones obtained by such method, was digested by SalI and SpeI at 37° C. for 2 hours, respectively. A fragment of ca. 6.7 kb length containing the 5' upstream region of human BMP-2 gene was identified by the conventional Southern blotting method using a primer shown in SEQ ID NO. 4 of the Sequence Listing. The fragment of SalI-SpeI was connected to the pBluescript vector having been treated with the same enzymes by using Takara Ligation Kit (a product of Takara Shuzo Ltd.). The vector was named $E.$ $coli$ P6.7B2 vector. The $E.$ $coli$ P6.7B2 was deposited in National Institute of Bioscience and Human-Technology, Agency of Industrial Science and Technology, Ministry of International Trade and Industry 1-3, Higashi 1-chome, Tsukuba-shi Ibaraki-ken 305-8566 Japan, in Mar. 30, 1998 with depository number FERM P-16735 and transferred to the International Depository Authority under Budapest Treaty on Feb. 17, 1999 (Deposit No. FERM BP-6649).

Example 2
Determination of DNA Sequence of Human BMP-2 Promoter

The sequence of the human BMP-2 promoter region was determined by ALF automatic DNA sequencer (a product of Amersham Pharmacia Biotech Ltd.) using P6.7B2 vector and a vector that was prepared by further subcloning of the inserted fragment of 6.7 kb of said vector as a template. Reading started from both ends was repeated at least three times. A site difficult in reading was subcloned to read the sequence starting from both ends. The sequence of ca. 6.7 kb promoter region and the structure thereof were shown in SEQ ID NO. 1 of the Sequence Listing and FIG. 1, respectively.

Figure 2:
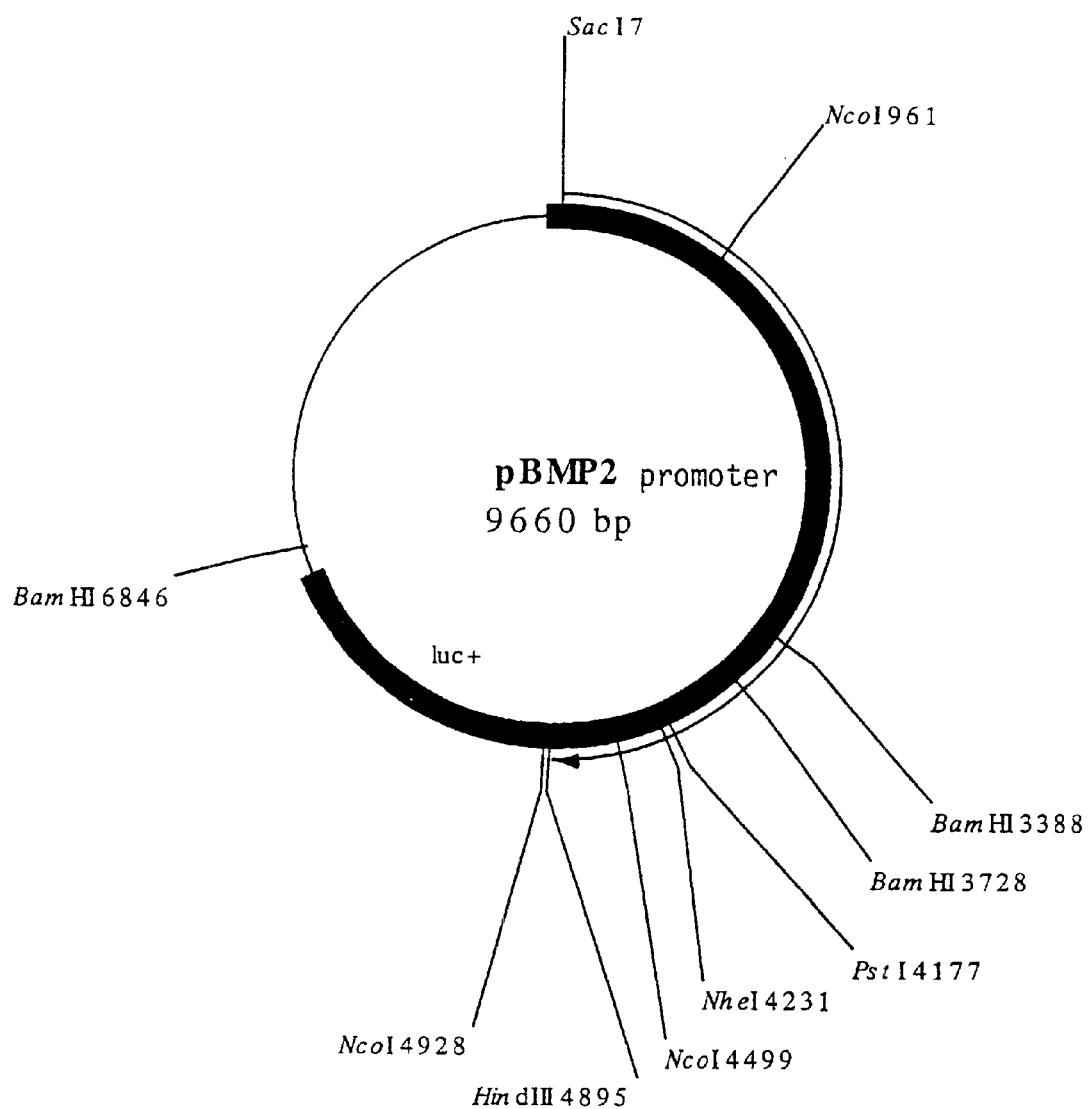
FIG. 2 is a recombinant expression vector (pBMP2) containing a 5' upstream region of human BMP-2 gene. A SmaI-SacI fragment (base No. from 482 to 5345 shown in SEQ ID NO. 1 of the Sequence Listing, referring to FIG. 1) was inserted to the restriction enzyme site of pGL3-basic.

Example 3
Construction of a Recombinant Expression Vector that Was Prepared by Connecting a Human BMP-2 Promoter to a Luciferase Reporter Gene NcoI-SmaI fragment of the 5' upstream region of the human BMP-2 gene containing a promoter region was connected to a pGEM5zf (+) vector (a product of Pro Mega Ltd.) digested by NcoI and EcoRV. The vector prepared was treated with NotI and ApaI restriction enzymes and connected to a pGEM11zf (+) vector (a product of Pro Mega Ltd.) prepared by treatment with the same enzymes. HindIII-SalI fragment of this vector was connected to a pGL3-basic vector (a product of Pro Mega Ltd.) treated with HindIII-XhoI. The vector obtained was treated with NcoI and BamHI and connected to a NcoI-BamHI fragment of the BMP-2 gene. Further, the vector obtained was treated with PstI and SacI and connected to a PstI-SacI fragment of the BMP-2 gene to obtain the aimed recombinant expression vector. The recombinant expression vector obtained was shown in FIG. 2. The recombinant expression vector pBMP2 (9660 bp) contains the 5' upstream region of ca. 5.1 kb of the human BMP-2 gene.

Example 4

Measurement of Activity of the Human BMP-2 Promoter

Figure 3:
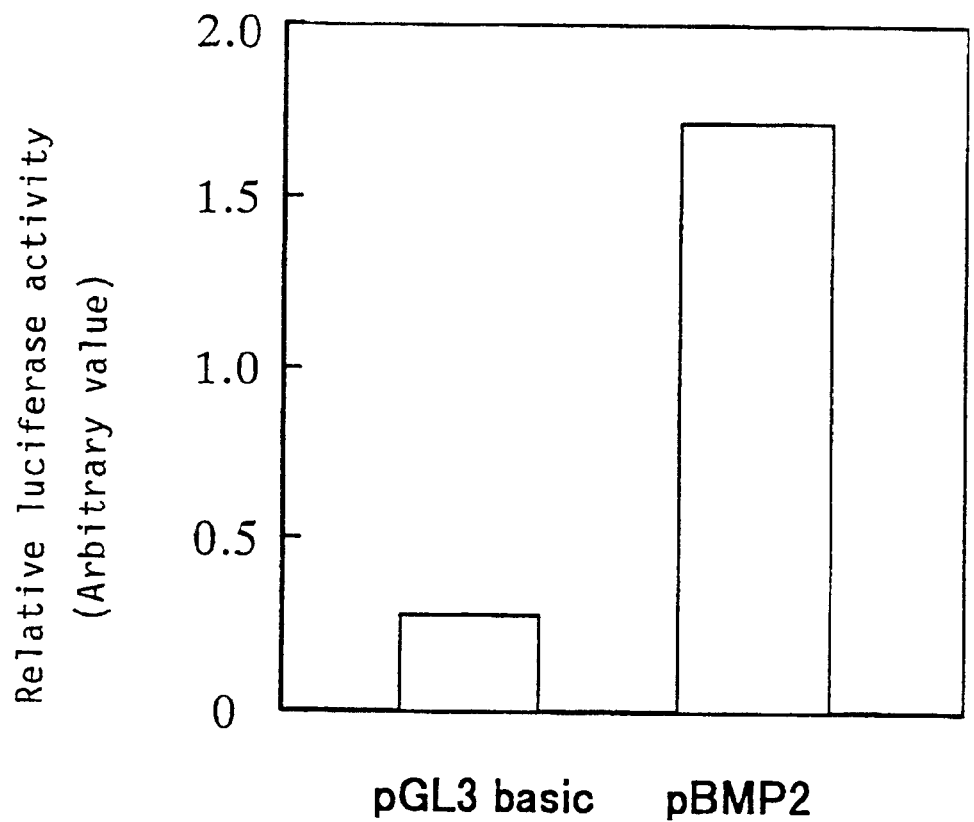
FIG. 3 is a result of measuring a human BMP-2 promoter activity (transiently expression).

In order to express transiently the recombinant expression vector pBMP2, above-described vectors were mixed with a vector, pRL-SV40 (a product of Pro Mega Ltd.) containing sea pansy luciferase gene as an internal control for measurement of efficiency of gene introduction in an equal quantity. Then, cationic liposome lipofectamine (a product of Lifetech Oriental Co.) was mixed with thus obtained to add to human osteosarcoma cells HOS for transfection. Fire fly luciferase activity and sea pansy luciferase activity were measured by Pikka Gene Dual Kit (a product of Toyo Ink Co.). The result is shown in FIG. 3. The longitudinal axis represents a promoter activity that was expressed as a ratio of fire fly luciferase activity to sea pansy luciferase activity. From the result, it has been known that the DNA of SEQ ID NO. 1 of the Sequence Listing has a promoter activity.

Example 5

Introduction of the Recombinant Expression Vector pBMP2 to a Human Cell and Stabilized Expression In order to express the recombinant expression vector pBMP2 stably, said vector was mixed with the vector pPUR (a product of CloneTech Ltd.) containing puromycin resistant gene in the proportion of 10:1 and also mixed with cationic liposome lipofectamine (a product of Lifetech Oriental Co.) and added to a human osteosarcoma cell HOS for transfection. The cells to which the aimed gene has been introduced were selected from a culture medium containing 0.5 μg/mL of puromycin (a product of Sigma Ltd.).

Example 6

Screening of an Active Low Molecular Weight Compound

Cells selected were inoculated in a 96-well plate, treated with substances of various chemical compound libraries for 1–3 days, dissolved with cytolytic agent (a product of Pro Mega Ltd.), and measured for enzyme activity by employing a luciferase assay kit (a product of Pro Mega Ltd.). By such processes, various substances inducing or inhibiting the expression of human BMP-2 can be explored.

What is claimed is:

1. An isolated DNA whose nucleotide sequence comprises nucleotides 1 to 6728 shown in SEQ ID No: 1, or a fragment thereof which is effective as a human bone morphogenetic protein-2 promoter.

2. A recombinant expression vector formed by integrating the DNA of claim 1 connected to a reporter gene into a vector.

3. A method of screening for a substance which regulates positively or negatively the expression of human bone morphogenic protein-2 comprising introducing a recombinant expression vector of claim 2 into a mammalian cell and measuring expression of the reporter gene in the presence of said substance to determine the effect of the substance on the human bone morphogenetic promoter region.

4. A mammalian cell containing the recombinant expression vector of claim 2.

5. A screening system for detecting substances which regulate positively or negatively the expression of human BMP-2 comprising a cell into which the recombinant expression vector of claim 2 has been introduced.

6. The method of claim 3, wherein the substance has bone or cartilage morphogenetic activity.

7. The method of claim 4, wherein the substance inhibits bone or cartilage morphogenesis.

8. The screening system of claim 5, wherein the cell is a mammalian cell and the recombinant expression vector is introduced using liposomes.

9. The screening system of claim 5, wherein the cell is a SaOS-2.

10. The screening system according to claim 5, wherein the recombinant expression vector contains a luciferase or β-galactosidase reporter gene.

11. A mammalian cell containing the isolated DNA of claim 1.

* * * * *

UNITED STATES PATENT AND TRADEMARK OFFICE
CERTIFICATE OF CORRECTION

PATENT NO.      : 6,475,735 B1
DATED           : November 5, 2002
INVENTOR(S)     : T. Sugiura It is certified that error appears in the above-identified patent and that said Letters Patent is hereby corrected as shown below:

<u>Column 14,</u>
Line 18, change "The method of claim 4" to read -- The method of claim 3 --

Signed and Sealed this

Twenty-second Day of July, 2003

JAMES E. ROGAN
*Director of the United States Patent and Trademark Office*